United States Patent [19]
Hood

[11] Patent Number: 5,352,230
[45] Date of Patent: Oct. 4, 1994

[54] PNEUMATIC IMPULSE TOOL

[75] Inventor: Larry L. Hood, Laguna Hills, Calif.

[73] Assignee: Biomet, Inc., Warsaw, Ind.

[21] Appl. No.: 837,649

[22] Filed: Feb. 19, 1992

[51] Int. Cl.$^5$ .............................. A61F 2/32; A61F 5/00
[52] U.S. Cl. ........................................ 606/99; 606/86; 606/100
[58] Field of Search .................... 606/100, 86, 87, 88, 606/89, 99, 101

[56] References Cited

U.S. PATENT DOCUMENTS

| | | | |
|---|---|---|---|
| 4,399,813 | 8/1983 | Bawber | 606/100 |
| 4,462,395 | 7/1984 | Johnson | 606/100 |
| 4,476,861 | 10/1984 | Dimakos | 606/100 |
| 5,057,112 | 10/1991 | Sherman | 606/100 |
| 5,108,400 | 4/1992 | Appel et al. | |
| 5,171,313 | 12/1992 | Salyor | 606/100 |

OTHER PUBLICATIONS

MicroAire ® Brochure, Feb. 1992.

Primary Examiner—Michael A. Brown
Attorney, Agent, or Firm—Knobbe, Martens, Olson & Bear

[57] ABSTRACT

A pneumatic inertia tool for applying a cyclic percussive force to an orthopedic article via a reciprocating shuttle comprising a passageway extending between a first port and a second port. The shuttle travels within the passageway and strikes an anvil, imparting its momentum to the orthopedic article. The mass of the shuttle and its velocity at impact are selected to fix a bone relative to the orthopedic article via the existing inertia of the bone. The shuttle reciprocates within the passageway by alternating pressure and vacuum forces applied at the first port and at the second port.

7 Claims, 8 Drawing Sheets

PNEUMATIC IMPULSE TOOL

BACKGROUND OF THE INVENTION

1. Field of the Invention

The present invention relates to a pneumatic impulse tool and, in particular, to a pneumatic impulse tool used to insert an orthopedic article into or extract an orthopedic article from a bone.

2. Description of Related Art

Artificial joints, such as hips, knees, shoulders, wrists, elbows and fingers, often attach to a structurally sound bone by a stem lodged in a cavity formed in the bone. For instance, in a hip joint replacement, a surgeon commonly removes a worn or diseased femoral neck. The surgeon then prepares the medullary canal using drills, reamers and successively larger rasps to produce a cavity which is closely complementary to a femoral stem of the prosthesis. After cleaning, the surgeon commonly drives the stem into the canal to produce what is essentially a press fit. In addition, the femoral stem may be held in place by a cement, such as polymethylmethacrylate (PMMA), or the stem may be provided with a porous surface on its shank which accommodates ingrowth of cancellous bone to secure the femoral prosthesis stem in the femur.

Orthopedic surgeons commonly use hammers or mallets to drive the femoral stem into the cavity, overcoming the opposing friction force. A surgeon using a hammer or mallet will inevitably vary the direction that the force is applied to the prosthesis, thereby increasing the chances of fracturing the surrounding cortical bone. Moreover, because of the force required to drive the prosthesis, brittle bones frequently break during the orthopedic procedure.

Despite advances in the technology of artificial joint replacement, a substantial number of "revisions" are required. Such revisions involve removing components of the artificial joint and replacing them. Again, surgeons commonly use hammers or mallets to extract the prosthesis, breaking the bond between the prosthesis and the bone ingrowth or PMMA cement. Consequently, the revisions are traumatic for the patient, tedious for the surgeon, and quite time consuming for the surgical staff and facilities.

To overcome the arduousness associated with using hammers during orthopedic surgery, pneumatic impact devices have been developed which apply a percussive force on an orthopedic article, such as a prosthesis or broach, to insert the orthopedic article into or extract the orthopedic article from a bone. In addition, pneumatic impact devices commonly apply the driving or extracting force along a consistent vector, thereby reducing the chances of fracturing the surrounding bone. Examples of such pneumatic impact devices are disclosed by U.S. Pat. No. 5,057,112, issued to Sherman, et al. ("the Sherman patent") and PCT International Publication No. WO8802246 ("the PCT publication").

Although the devices disclosed by these references overcome some of the aforementioned disadvantages associated with hammers and mallets, these devices are little improvement over hammers and mallets in the sense of reducing trauma in the bone surrounding the orthopedic article. For instance, the device disclosed by the PCT publication does not significantly reduce the trauma experienced by the patient during the orthopedic procedure. As the piston strikes the distal end of the cavity, the entire mass of the housing and the piston act on the orthopedic article attached to the device, much like a large hammer.

Moreover, these devices are unduly complicated and costly to produce. For instance, the pneumatic impact tool disclosed by the Sherman patent uses an internal shutter valve and a series of complicated ducts to reciprocate a piston within a cylindrical cavity. Likewise, the pneumatic impact tool of the PCT publication comprises a plurality of intricate channels formed within a handle of the tool. Because of the costs associated with producing these devices and because of the short useful life pneumatic impact tools commonly provide, these devices are mainly limited to clinical environments.

Finally, most pneumatic tools used in operating rooms commonly require dedicated tanks of pressurized gases, such as compressed air or nitrogen, as a pneumatic pressure source. However, pressure tanks present a hazard for the surgical staff.

Thus, a need exists for a simple pneumatic impact tool which minimizes the trauma the patient experiences when inserting an orthopedic article into or extracting an orthopedic article from a bone.

SUMMARY OF THE INVENTION

The present invention includes the recognition that by striking an orthopedic tool with sufficient force to overcome opposing forces and rapidly transferring that force to the orthopedic article, the host bone and surrounding limb will remain substantially stationary, fixed by their own inertia. Less force is therefore transferred to the host bone as the orthopedic article is inserted into or extracted from the host bone. Consequently, a patient experiences less trauma during orthopedic surgery using an apparatus embodying the invention than a patient currently experiences during orthopedic surgery using prior tools, such as those discussed above.

Through empirical and analytical analysis, it has been determined that if an impulse force, having a peak force equal to about 1.5 times the opposing force, is applied to the orthopedic article over a contact period (i.e., the period of contact between a driving article and the orthopedic article or attached extender) equal to less than 300 micro-seconds ($\mu$sec.) and if the impulse force rises to its peak force within a period (i.e., "rise time") equal to less than 100 $\mu$sec., then the force transferred from the orthopedic article to the host bone would be equal to or less than one-fifth (1/5) of the impulse force. The impulse force more preferably has the characteristics of a rise time equal to less than 10 $\mu$sec. and a total contact time equal to less than 30 $\mu$sec. Consequently, the bone and surrounding limb senses less of the driving force applied to the orthopedic article and less trauma results during the orthopedic procedure.

In accordance with another aspect of the present invention, there is provided an apparatus for applying a percussive force to an orthopedic article which is adapted for use in an operating room having existing pneumatic pressure and vacuum sources. Operating rooms of hospitals and clinics commonly includes a pneumatic pressure line supplying about 70 pounds of pressure per square inch (psi) and a vacuum line drawing about 15 psi. Hospitals and clinics usually limit the pneumatic pressure and vacuum sources to these levels within operating rooms because of safety considerations. Moreover, most countries, through government or industry organizations, impose limits on pressure levels of fluids within operating rooms. For instance, in the United States, the United Laboratories (UL) limits compressed fluids in an operating room to 170 psi (regulation UL-544).

One embodiment of the inventive apparatus includes a housing defining a central cavity between a distal end and a proximal end. The proximal end of the central cavity selectively communicates with a first pressure source and the distal end selectively communicates with a vacuum source. The apparatus additionally includes a shuttle which is positioned within the central cavity and is configured to travel between the proximal end and the distal end of the central cavity. By applying a pressure source at the proximal end and a vacuum at the distal end, a driving pneumatic force produced by the pressure differential within the central cavity across the shuttle is maximized.

In accordance with another aspect of the invention, an impulse apparatus includes an exterior tube concentrically positioned around a smaller central tube to form a duct between the two tubes. A shuttle is placed within a central cavity defined by the central tube and is configured to slide within the cavity. The apparatus additionally includes a first end plug and a second end plug. The first end plug seals on set of ends of the concentric tubes and the second end plug seals the other set of ends of the concentric tubes, thereby enclosing the shuttle within the cavity of the central tube. The first end plug includes a first passageway which communicates with the cavity of the central tube and a second passageway which communicates with the duct formed between the concentric tubes. The second end includes a passageway which extends between the central cavity and the duct. The apparatus additionally includes a drive coupling having an anvil which extends into the central cavity. The drive coupling is also preferable configured to couple with the orthopedic article.

In accordance with one preferred method of generating a net pulling or pushing force in a reciprocating mass hammer of the type having a housing with a first and a second port thereon and a passageway extending therebetween, the pressure at the first port is elevated while the pressure at the second port is simultaneously reduced to move a mass within the passageway towards an anvil of the reciprocating mass hammer. The method further includes the step of either reducing the pressure at the first port or elevating the pressure at the second port to separate the mass and anvil.

BRIEF DESCRIPTION OF THE DRAWINGS

These and other features of the invention will now be described with reference to drawings of a preferred embodiment which is intended to illustrate and not to limit the invention, and in which:

FIG. 5 is a cross-sectional view of a distal end plug of the pneumatic impulse tool taken along line 5—5 of FIG. 2a;

DETAILED DESCRIPTION OF THE PREFERRED EMBODIMENT

Figure 1:
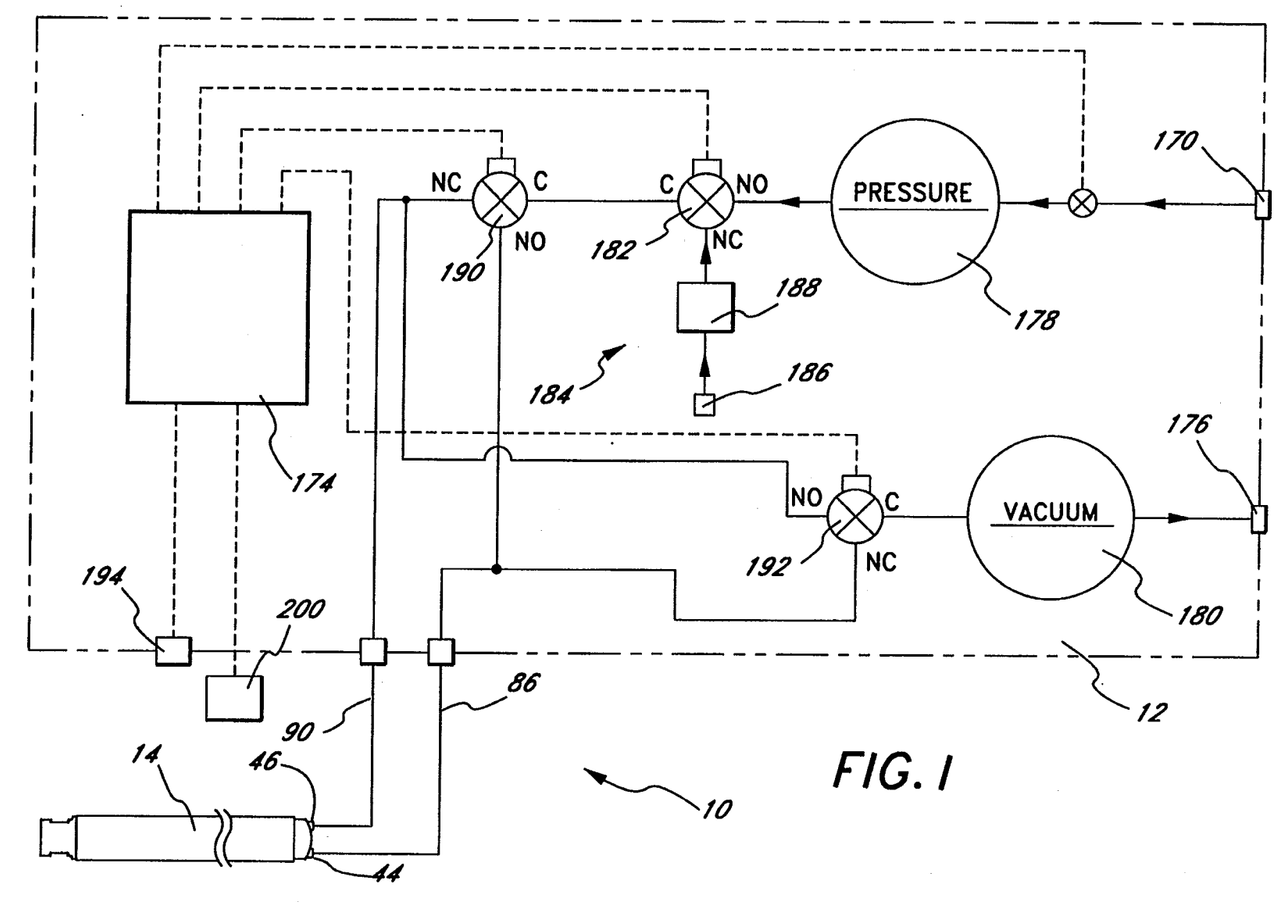
FIG. 1 is a schematic illustration of a pneumatic impulse apparatus in accordance with a preferred embodiment of the present invention.

FIG. 1 schematically illustrates a pneumatic impulse apparatus 10 comprising a pneumatic control unit 12 connected to a pneumatic impulse tool 14. The impulse tool 14 is used to insert an orthopedic article (such as, for example, a prosthesis, broach, rasp, tool bit, rod or the like) into a bone or to extract an orthopedic article from a bone.

The streamline, symmetric configuration of the impulse tool 14 makes the it extremely maneuverable within the tight confines of an orthopedic surgical site. Additionally, the impulse tool 14 has a simple internal pneumatic flow-passage principally formed between two concentric tubes. In spite of its simplicity, the impulse tool 14 does not exhaust its working fluid (i.e., air) into the surgical field, thereby maintaining the sterility of the surgical field.

Figure 2:
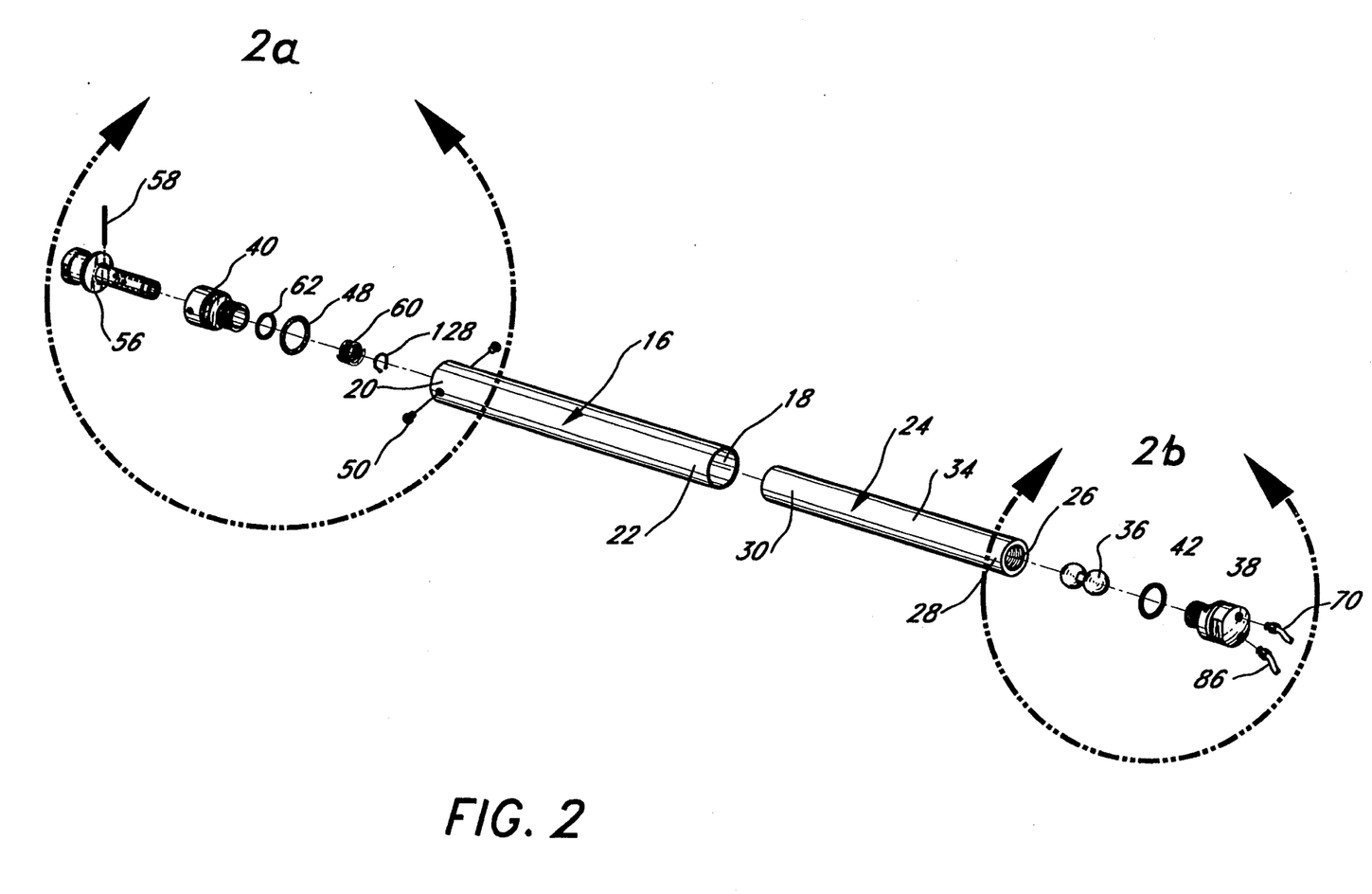
FIG. 2 is an exploded perspective view of an impulse tool of the pneumatic impulse apparatus of FIG. 1.
Figures 2A, 2B:
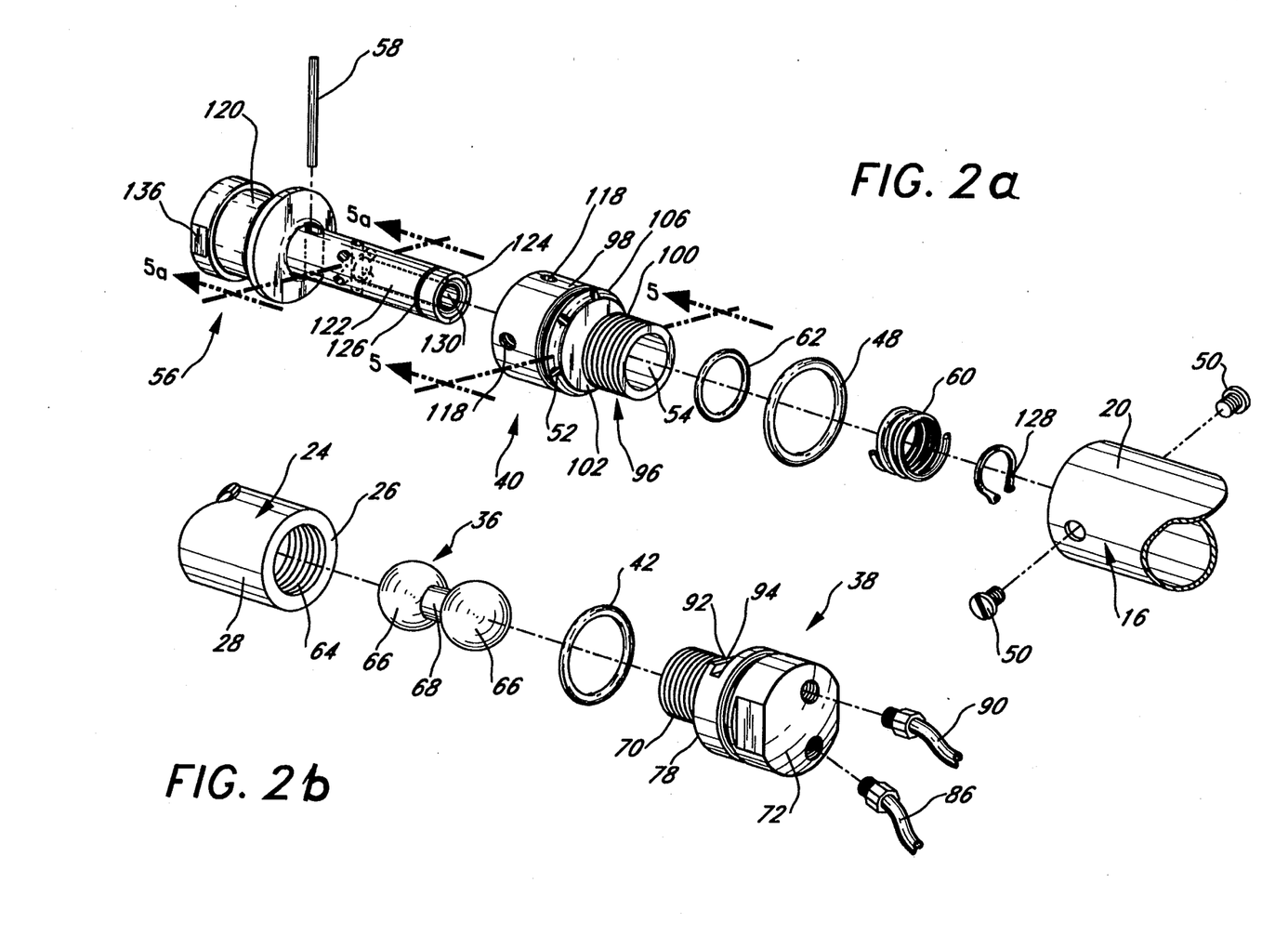
FIG. 2a is an enlarged perspective view of the area within line 2a of FIG. 2.
FIG. 2b is an enlarged perspective view of the area within line 2b of FIG. 2.

Referring to FIGS. 2, 2a and 2b, the pneumatic impulse tool 14 comprises a cylindrical exterior tube 16 having an interior surface 18 extending between a distal end 20 and a proximal end 22. As used herein, the words "proximal" and "distal" are used in reference to the proximity of the pneumatic control unit 12 which supplies pneumatic pressure to the pneumatic impulse tool 14. Thus, the impulse tool 14 couples to an orthopedic article at its distal end.

A central tube 24 defining a cylindrical central cavity 26 between a proximal end 28 and a distal end 30, is inserted into the exterior tube 16, creating a duct 32 between an exterior surface 34 of the central tube 24 and the interior surface 18 of the exterior tube 16, as will be discussed below.

Figure 3:
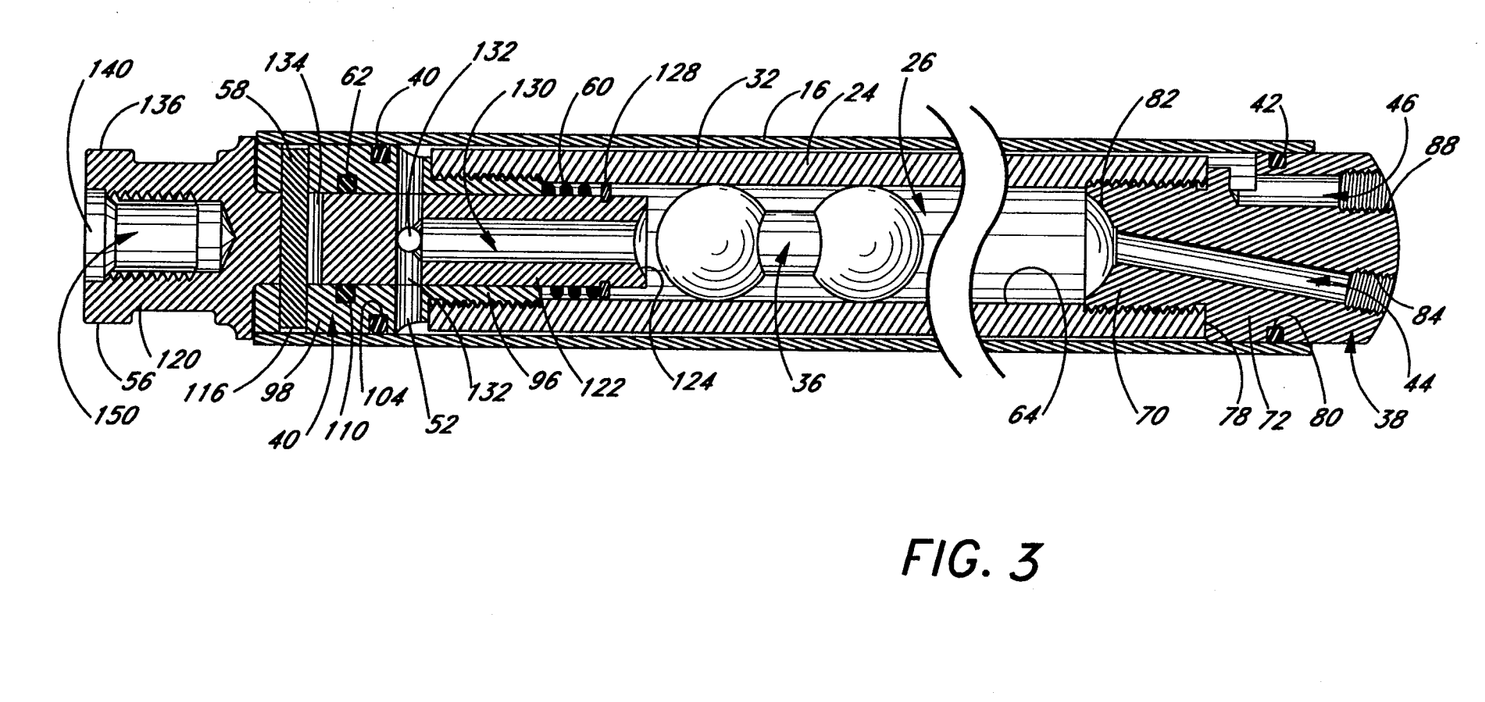
FIG. 3 is an assembled cross-sectional view of the impulse tool of FIG. 2.

As illustrated in FIGS. 2 and 3, a shuttle 36 is placed within the central cavity 26 and is enclosed therein between a proximal end plug 38 and a distal end plug 40. The proximal end plug 38 attaches to the central tube proximal end 28. An O-ring 42 is placed between the interior surface 18 of the exterior tube 16 and the proximal end plug 38 to seal the duct 32 from the atmosphere. The proximal end plug 38 defines a first port 44 in communication with the central cavity 26 and a second port 46 in communication with the duct 32.

The distal end plug 40 connects to the central tube distal end 30. The exterior tube 16 is held to the distal end plug 40 via a plurality of screws 50 extending in the radial direction. An O-ring 48, disposed between the distal end plug 40 and the interior surface 18 of the exterior tube 16, hermetically seals the duct 32 from the atmosphere, thereby preventing accidental leaks of the working fluid into the sterile surgical field.

The duct 32 communicates with the central cavity 26 via a plurality of radially extending channels 52 within the distal end plug 42. The distal end plug 40 further defines a central bore 54 which receives a drive coupling 56.

The drive coupling 56 extends from the distal end of the impulse tool 14 into the central cavity 26 through the distal end plug 40. A dowel pin 58 couples the drive coupling 56 to the distal end plug 40 by extending through an aligned pair apertures defined by the drive coupling 56 and the distal end plug 40, and a spring 60 biases the driving coupling 56 in the proximal direction. An O-ring 62 hermetic seals the central cavity 26 from the surgical field between the drive coupling 56 and the distal end plug 40.

In use, the impulse tool 14 receives pneumatic pressure from the pneumatic control unit 12 alternating through the first port 44 and the second port 46 of the proximal end plug 38, as described in greater detail infra. The alternating pneumatic pressure causes the shuttle 36 to reciprocate within the central cavity 26, striking the proximal end plug 38 and the drive coupling 56. That is, pressure applied through the first port 44 during a first half of the reciprocating cycle, propels the shuttle 36 in the distal direction; pressure applied through the second port 46 during the second half of the reciprocating cycle, propels the shuttle 36 in the proximal direction. By applying greater pressure through the first port 44 than through the second port 46 during the reciprocating cycle, the pneumatic impulse tool 14 drives an attached orthopedic article in the distal direction. Conversely, by applying greater pressure through the second port 46 than through the first port 44 during the reciprocating cycle, the pneumatic impact tool 14 extracts the orthopedic article from the bone in the proximal direction. The individual components of the pneumatic impulse tool 14 will now be described in detail. Descriptions of the pneumatic control system 12 and the operation of the pneumatic impulse apparatus 10 will follow thereafter.

Pneumatic Impulse Tool

FIG. 2 illustrates in an exploded perspective view the components of a preferred embodiment of the pneumatic impulse tool 14 and FIGS. 2a and 2b illustrate the components of the distal and proximal ends of the impulse tool 14, respectively. FIG. 3 illustrates a cross-sectional assembly view of the pneumatic impulse tool 14. The components of the impulse tool 14 will now be described with reference to these drawings.

Central and Exterior Tubes. The exterior tube 16 has a length slightly longer than the central tube 24 which is sized to provide the shuttle 36 with a sufficient length of travel to achieve a desired impact velocity, as will be discussed in detail infra. The exterior tube 16 has a length preferably ranging between 6.0 inches and 36.0 inches, more preferably ranging between 9.0 and 24.0 inches, and most preferably equaling approximately 18.0 inches. The central tube 24 is preferably 1.0 to 2.0 inches shorter than the exterior tube 16 and is internally threaded at its distal and proximal ends 28, 30 to engage the end plugs 38, 40.

The central tube 24 has an inner diameter (i.e., the diameter of the central cavity 26) sufficiently sized to receive a shuttle 36 having a desired mass M in accordance with the parameters discussed below. Advantageously, the central tube 24 is sized slightly larger that the diameter of the shuttle 36 such that an air boundary forms as the shuttle 36 travels over the interior surface 64 defining the central cavity 26. The resultant air boundary acts as an bearing surface, reducing friction between the central tube 24 and the shuttle 36, as known in the art. The central tube 24 preferably has an interior diameter sized 0.008+0.003 inch larger than the diameter of the shuttle 36. The interior surface 64 of the central tube 24 additionally may be coated with a solid lubricant to further reduce friction between the shuttle 36 and the central tube 24.

The exterior tube 16 has an inner diameter sufficiently sized to minimize the fluidic resistance in the duct 32 formed between the exterior tube 16 and the central tube 24. Preferably, the exterior tube 16 has an inner diameter at least 0.050 of an inch larger that the exterior diameter of the central tube 24.

In a preferred embodiment, the central tube 24 comprises a seamless 440 A stainless steel tube having an nominal inner diameter equal to about 0.508 inch and an outer diameter equal to about 0.750 inch; however, the central tube 24 could comprise any rigid material with a yield strength similar to that of stainless steel. The length of the central tube 24 is about 16.0 inches such that the shuttle 36 has a travel through the central cavity 26 of about 13.0 inches.

The exterior tube 16 preferably is constructed from a composite of plastic materials to reduce the percussive sound emanating from the central cavity 26. In a preferred embodiment, the exterior tube is formed from a composite made of a lightweight plastic, such as, for example, tetrafluoroethylene (teflon), sandwiched between a layers of a heaver plastic, such as, for example, polyvinylchloride (PVC).

Shuttle. Referring to FIG. 3, the shuttle 36 is configured to reduce friction between the shuttle 36 and the central cavity wall 64 and is sized to minimize the force transferred between the orthopedic article and the host bone. That is, the mass M of the shuttle is selected to minimize the impact force transferred to the bone, as will be discussed in detail infra.

In a preferred embodiment, the shuttle 36 has a barbell-shape comprising a pair of identical spheres 66 tied together by a cylindrical cross member 68. The spheres 66 advantageously have a diameter smaller than the inner diameter of the central tube 24 to create an air bearing surface, as discussed above. The spheres 66 preferably comprise 400 series stainless steel (e.g. 440 C Stainless Steel), precision ball bearings having a Rockwell C hardness of 60 to 65. The spheres 66 preferably have a diameter ranging between 0.125 inch and 3.0 inch, more preferably ranging between 0.500 inch and 1.000 inch, and most preferably having a diameter equal to about 0.500 inch.

The cross member 68 has a diameter sized significantly smaller than the diameters of the spheres 66. Consequently, only the peripheral portions of the spheres 66, which are generally perpendicular to a longitudinal axis of the central tube 24, juxtapose the interior surface 64 of the central tube 24. Thus, the surface contact between the shuttle 36 and the central tube 24 is minimized to reduce friction.

The overall length of the shuttle 36, like its overall diameter, depends upon the shuttle mass M desired according to the parameters discussed below. In a preferred embodiment, the length of the shuttle is less than 5.0 inches, preferably ranges between 0.5 inch and 3.0 inches, more preferably ranges between 1.0 inch and 2.0 inch, and most preferably equals about 1.5 inch.

Proximal End Plug. As illustrated in FIGS. 2a and 3, the proximal end plug 38 comprises a shank 70 extending from a generally cylindrical body 72. The shank 70 includes external threads 74 which engage the internal threads of the central tube proximal end 28. At its distal end, the shank 70 defines a concave anvil surface 76 having an arcuate shape complementary to the spherical shape of the shuttle sphere 66.

The cylindrical body 72 of the proximal end plug 38 is sized to snugly fit within the exterior tube 16. The diameter of the cylindrical body 72 preferably is less than 0.100 inch smaller, more preferably less than 0.010 inch smaller, and most preferably less than 0.004 inch smaller than the inner diameter of the exterior tube 16. The cylindrical body 72 terminates in the distal direction in an annular abutment surface 78 which circumscribes the threaded shank 70. The abutment surface 78 has a diameter sized approximately equal to the outer diameter of the central tube 24. The abutment surface 78 adjoins the proximal end 28 of the central tube 24 when assembled together. The cylindrical body 74 also defines an annular groove 80 which received the O-ring 42 when assembled.

The proximal end plug 38 defines the first port 44 which extends from the proximal end of the proximal end plug 38, through the cylindrical body 72 and shank 70, and to the concave anvil surface 76. The opening 82 of the first port 44 at the anvil surface 76 preferably lies generally at the center of the central cavity 26 to maximize the pneumatic force initially applied to the shuttle 36 and to evenly distribute pneumatic pressure around the shuttle 36 for the desired air bearing effect.

The first port 44 preferably has a linear configuration to minimize fluidic resistance through the port 44. On its proximal side, the first port 44 includes an internal threaded portion 84 which engages with a pneumatic coupling of a first pneumatic line 86.

The proximal end plug 38 additionally defines the second port 46 which also extends from the proximal end of the proximal end plug 38 into the cylindrical body 72. The second port 46 includes an internal threaded portion 88 proximate to its proximal end which engages with a complementary threaded male connector of a second pneumatic line 90. The second port 46 opens onto the exterior of the cylindrical body 72 at a position between the annular groove 80 and the abutment surface 78. The second port 46 communicates with the duct 32 formed between the concentric tubes 16, 24 and desirably has a sufficient size to minimize fluidic resistance through the port 46. The second port 46 preferably has a diameter ranging between 0.050 inch and 0.50 inch, more preferably has a diameter generally equaling to about 0.25 inch, and most preferably a diameter equaling to about 0.125 inch.

Figure 4:
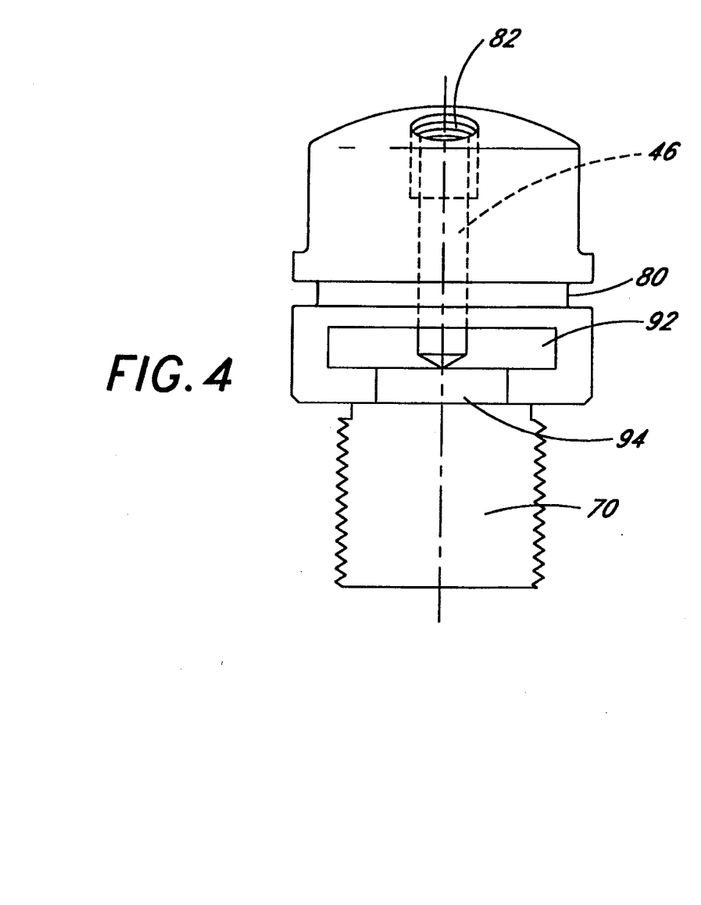
FIG. 4 is a top plan view of a proximal end plug of the pneumatic impulse tool of FIG. 1.

Referring to FIGS. 2a, 3 and 4, the second port 46 opens into a funneling channel 92 which extends between the periphery of the cylindrical body 72 and the second port 46. The cylindrical body 72 further defines a relief 94 adjacent to and distal of the funneling channel 92 which forms a passageway between the duct 32 and the funneling channel 92 when assembled with the exterior tube 16. The funneling channel 92 and the relief 94 are preferably sized to reduce fluidic resistance from the duct 32 to the second port 44.

Distal End Plug. Referring to FIG. 2b, the distal end plug 40 also comprises a shank 96 extending from a generally cylindrical body 98. The shank 96 includes an external thread 100 which engage the internal threads of the central tube distal end 30. The cylindrical body 98 is sized to snugly fit within the exterior tube 16. The diameter of the cylindrical body 98 preferably is about 0.100 inch smaller, more preferably about 0.010 inch smaller, and most preferably about 0.004 inch smaller than the inner diameter of the exterior tube 16.

The cylindrical body 98 terminates in the proximal direction in an annular abutment surface 102 which circumscribes the threaded shank 96. The abutment surface 102 has a diameter sized approximately equal to the outer diameter of the central tube 24. The abutment surface 102 adjoins the distal end 30 of the central tube 24 when assembled together. The cylindrical body 98 also defines an annular groove 104 which receives the O-ring 48 when assembled. The cylindrical body 98 further includes a transition section 106 which tapers in diameter from the diameter of the cylindrical body 98 to the diameter of the abutment surface 102.

The cylindrical bodies 98, 72 of the distal end plug 40 and the proximal end plug 38 have lengths longer than one-half of the difference between the lengths of the central tube 24 and the exterior tube 16. As a result, when assembled with the tubes 16, 24, the cylindrical bodies 72, 98 of the end plugs 38, 40 extend beyond the ends of the exterior tube 16.

The distal end plug 40 additionally defines a central bore 54 which extends through the distal end plug 40 in the longitudinal direction. The central bore 54 is preferably concentrically positioned about the longitudinal axis of the distal end plug 40. The distal end plug 40 further defines an annular groove 110 extending into an interior wall 112 defining the central bore 54 which receives the O-ring 62 when assembled.

The distal end plug 40 further defines a dowel pin hole 116 extending through the cylindrical body 98 in a direction transverse to the longitudinal axis of the distal end plug 40. The distal end plug 40 also includes a plurality of tapped holes 118 equally spaced about the circumference of the cylindrical body 98 within the same transverse plane defined by the dowel pin hole 116. The tapped holes 118 receive a plurality of screws 50 which hold the exterior tube 16 in place.

Figure 5:
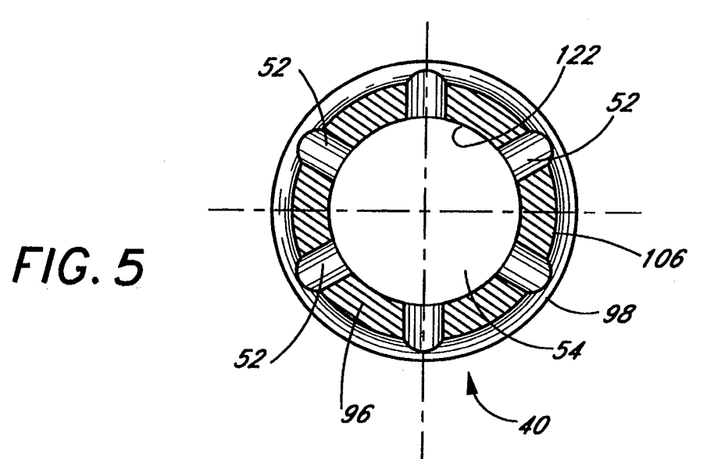

As illustrated in FIGS. 2b and 5, the distal end plug 40 further defines the plurality of channels 52 which extend in the radial direction from the longitudinal axis of the distal end plug 40 in a spoke-like fashion. Although FIG. 5 illustrates the distal end plug 40 defining six channels 52, it is understood that the distal end plug 40 should define at least one channel 52 and should not define too many channels 52 so as to degrade its structural integrity.

Each channel 52 extends between the central bore 54 and the periphery of the transition surface 106 of the cylindrical body 98. The channels 52 thus open onto the exterior of the cylindrical body 98 at a position between the annular groove 104 and the abutment surface 102. When assembled with the central tube 24 and the exterior tube 16, the channels 52 communicate with the duct 32 formed between the concentric tubes 16, 24. The channels 52 desirably have a sufficient size to minimize fluidic resistance between the central cavity 26 and the duct 32. Each channel 52 preferably has a diameter ranging between 0.050 inch and 0.50 inch, more preferably has a diameter equal to about 0.25 inch, and most preferably has a diameter equal to about 0.125 inch. Alternatively, the channels 52 may comprise long slots to reduce the fluidic resistance within the pneumatic impact tool 14.

Drive Coupling. FIGS. 2b and 3 illustrate the drive coupling 56 comprising an engagement head 120 and a cylindrical anvil 122. The cylindrical anvil 122 has a diameter sized slightly smaller that the central bore 54 diameter of the distal end plug 40 such that the anvil 122 slides within the central bore 54. The anvil 122 defines at its proximal end a concave anvil surface 124 having a spherical radius generally complementary to the shape of the shuttle sphere 66. The anvil 122 also defines an annular groove 126 positioned proximate to the proximal end of the anvil 122 and sized to receive a retainer ring 128 used to secure the return spring 60 in place. The return spring 60 may comprise a helical compression spring or a Belleville spring stack.

Figure 5A:
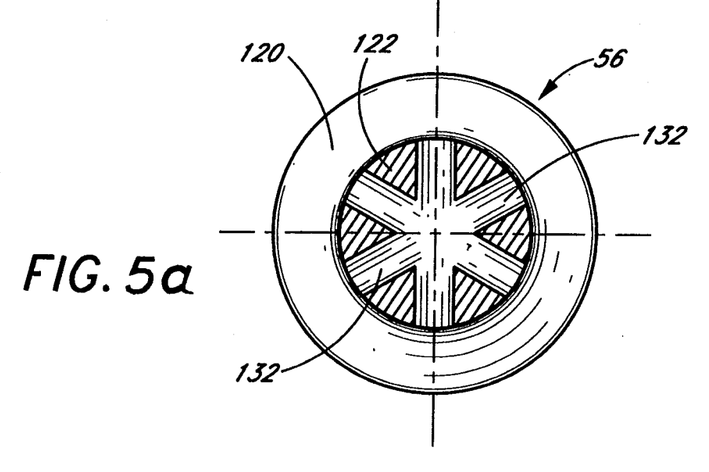
FIG. 5a is a cross-sectional view of a driving coupling of the pneumatic impulse tool taken along line 5a—5a of FIG. 2a, illustrating with FIG. 5 the alignment of internal flow paths within the distal end plug and the drive coupling.

Referring to FIGS. 2b, 5 and 5a, the anvil 122 additional defines a flow path between the anvil surface 124 positioned in the central cavity 26 and the duct 32 formed between the central tube 24 and the exterior tube 16. Specifically, the anvil 122 defines a central channel 130 and a plurality of radially extending channels 132, each of which is positioned to directly communicate with a radial channel 52 of the distal end plug 40. The central channel 130 extends into the anvil 122 from the concave anvil surface 124 along the longitudinal axis of the anvil 122. The central channel 130 terminates at an intersection of the plurality of radial channels 132. Each radial channel 132 extends generally from the longitudinal axis of anvil 122 to the anvil's periphery. The number of radial channels 132 is equal to the number of radial channels 52 of the distal end plug 40. When the drive coupling 56 and distal end plug 40 are assembled together, each anvil radial channel 132 generally aligns with a distal end plug radial channel 52, thereby forming a flow path between the anvil central channel 130 and the duct 32 formed between the central tube 24 and the exterior tube 16.

The anvil 122 further defines a transverse slot 134 which receives the dowel pin 58 used to secure the anvil 122 within the central bore 54. The transverse slot 134 is preferably sized larger that the dowel pin 58 to permit the anvil 122 to slide within the central bore 54. The transverse slot 134 is preferably sized such that the anvil 122 has a travel ranging between 0.005 inch to 0.250 inch, more preferably ranging between 0.010 inch to 0.100 inch, and most preferably equaling 0.050 inch. When assembled together, the dowel pin 58 limits forward travel of the anvil 122 (i.e., travel in the distal direction), stopping the anvil 122 before the return spring 60 bottoms out. In addition, the dowel pin 60 maintains alignment between the radial channels 132 of the anvil 122 and the radial channels 52 of the distal end plug 40. The dowel pin 60 also limits the throw of the impulse tool 14 when driven in the proximal direction.

Figure 6:
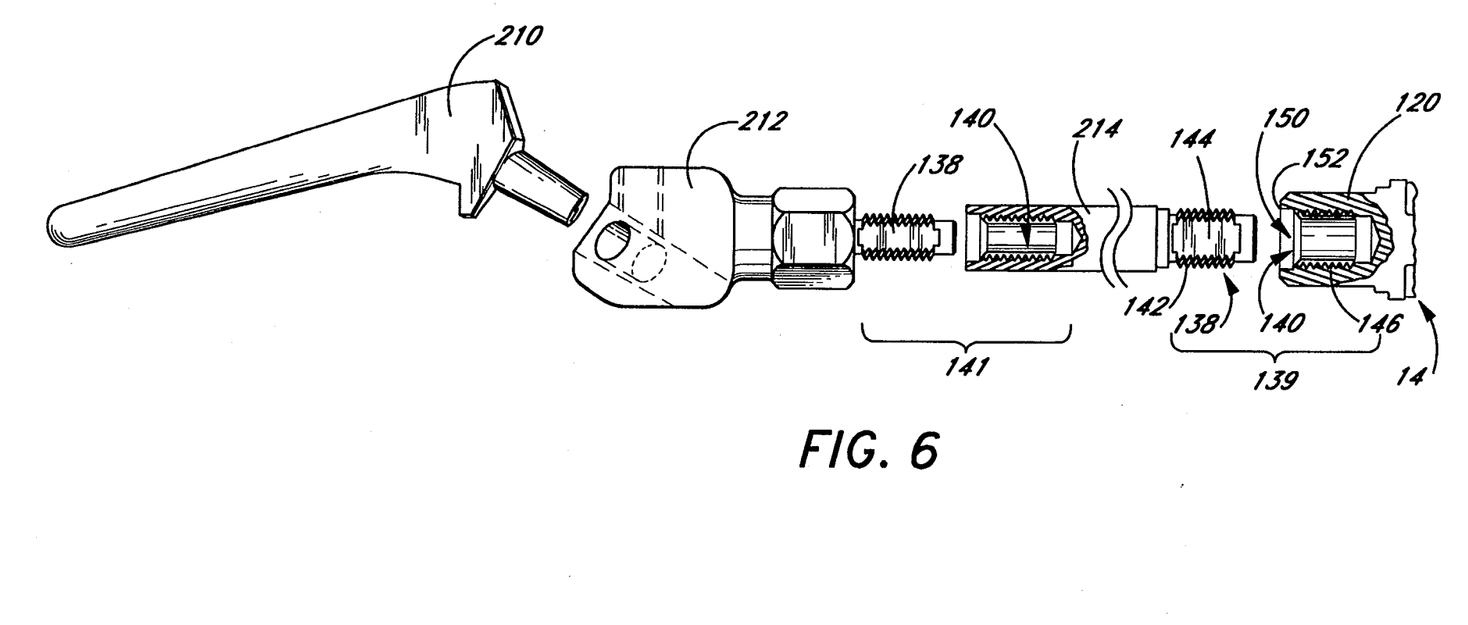
FIG. 6 is an exploded partial cut-away side elevational view illustrating a conventional prosthesis, an adapter, an extender and a distal end of the pneumatic impulse tool of FIG. 1.

The engagement head 120 of the drive coupling 56 has a generally cylindrical configuration interrupted by a pair of wrenching flats 136 disposed diametrically opposite one another. The engagement head 120 additionally includes a junction component adapted to receive a corresponding junction component. As illustrated in FIG. 6, the engagement head 120 preferably comprises a quick connecting junction component which quickly connects with the corresponding component by inserting a male component 138 into a female component 140 and rotating one component with respect to the other component, preferably through a relatively short rotational arc, and optimally about 90°±10°. As a result, the force applied by the impulse tool 14 efficiently transfers across the junction 139 and the impulse tool 14 is quickly disconnected from the orthopedic article without wrapping-up the connected pneumatic lines 86, 90 (FIG. 1).

Although FIG. 6 illustrates the engagement head 120 comprising the female component 140 extending in a proximal direction, it is understood that the relationship of the male and female components can be reversed. That is, the engagement head 120 could comprises a male component 138 extending in the distal direction.

Referring to FIG. 6, the impulse tool 14 connects to an extender 214 via a first junction 139. Likewise, the extender 214 connects to an adapter 212 via a second junction 141. It is contemplated that the components of the first and second junction 139, 141, will be substantially identical, and the discussion herein of one junction will be understood as applying equally to both.

The male component 138 comprises at least two axially extending splines 142 spaced apart by at least two axially extending flats 144. Preferably, the male component 138 comprises two diametrically opposed splines 142 and two diametrically opposed flats 144, alternatively positioned around the circumference of the component.

Each spline 142 comprises a plurality of external threads preferably configured in accordance with the American National Standard for Unified Threads ("UN"). It will be understood that other thread configurations, such as the American National Standard Acme Screw Threads ("Acme"), can be used as well. It has been found preferable, however, to use the UN thread design instead of others, such as the Acme thread design, primarily for manufacturing ease.

Advantageously, the thread pitch and the pitch diameter of the threads and the length of the splines 142 are selected to produce high axial compression between the components 138, 148 without structural failure. The components 138, 140 preferably produce an axial compressive force of about 3000 lbs. across the junction. It is also preferable to select a generally standard thread for manufacturing convenience. Additionally, the threads must engage to produce high axial compression with little rotation. Preferably, circumferentially, 75% of the threads engage with rotation of no more than about 90° plus or minus 10°. For example, in one preferred embodiment the splines 142 comprise a series of ¼-28 UNS-2A threads along a length of 0.435 inches, and in another embodiment, the splines 142 comprises a series of ⅜-28 UNF-2A threads along a length of 0.500 inches. In general, the spline 138 preferably comprises about 12 interrupted threads.

The junction generally has a minimum of 45° of total engagement between the spline threads to produce the high axial compression without mechanical failure. Preferably, the junction has an engagement between about 90°179° and most preferably about 173° (48% of 360°=172.8°). Thus, in a most preferred embodiment, the sum of the lengths of the threads on the male component 138 measured in a circumferential direction preferably range from 90° to 179°, and more preferably equal 173°.

The circumferential length of each spline thread (i.e., the circumferential width of each spline 142) depends upon the number of splines 142 employed. For example, in a most preferred embodiment having two splines, the length of the thread in a single spline 142 along the circumferential direction range between 45° and 89.5° and preferably equal 86.5°.

The female component 140 likewise comprises at least two axially extending splines 146 and at least two axially extending flats 148, disposed on the recess 150 circumference in a corresponding relationship with the flats 144 and splines 142 on the male component 138, as seen in FIG. 6. Preferably, the female component 140 comprises two diametrically opposed splines 146 and two diametrically opposed flats 148 alternatively positioned around the circumference of the recess 150. Each spline 146 comprises a plurality of internal threads configured to match and engage with the threads on the male component 138.

As discussed above, the sum of the length of the threads around the circumference of the recess 150 is preferably not less than about 90° and not greater than about 179°, and most preferably equal 173°. Each spline thread length depends upon the number of splines 146 employed. For example, in a most preferred embodiment having two splines 146, the threads of each spline 146 extend around the circumference of the recess 150 for at least approximately 45°, but less than approximately 89.5°, and preferably equal 86.5°.

The two splines 146 and two flats 148 alternately disposed on the interior circumference of the female component recess 150 provide an axial key-way for receiving the two opposing splines 142 on the male component 150. The male component 138 is inserted into the recess 150 of the female component 140 and rotated to interlock the corresponding splines 142, 146 on the male and female components 138, 140. It is desired that minimum rotation of one component with resect to the other component will produce a junction which achieves a relatively high efficiency of energy transmission therethrough.

The female component 138 preferably additionally comprises an annular engagement surface 152 on the distal end thereof which contacts a corresponding annular engagement surface 154 of the male component 138. Preferably, the engagement surface 154 of the female component 140 extends radially outwardly along a plane substantially perpendicular the axis of the internal recess 150, and the engagement surface 154 of the male component 138 extends radially outward along a plane substantially perpendicular to the axis of the male component 138. As the splines 142, 146 interlock, the two components 138, 140 draw together to force the engagement surfaces 152, 154 against each other, resulting in an axial compression force across the junction. Preferably, the engagement surfaces 152, 154 are smoothly polished to produce a substantially liquid-tight seal between the components 138, 140 as the surfaces 152, 154 abut.

Additionally, the junction components 138, 140 can be designed for use with ultrasonic equipment, as is disclosed in co-pending patent application Ser. No. 07/665,418, which is hereby incorporated by reference.

The proximal end plug 38, the distal end plug 40 and the drive coupling 56 can be manufactured from any of a variety of materials known in the art. Preferably, a stainless steel, such as a 400 series (e.g., 440 A) or 17-4 series stainless steel, is used because of its relative biocompatibility and its high yield strength.

Pneumatic Control System

Referring to FIG. 1, the pneumatic control system 12 controls and powers the impulse tool 14. The pneumatic control system 12 comprises a pneumatic input port 170 which connects to a standard pneumatic pressure supply line in a hospital or clinic operating room. The input port 170 is connected to a pressure regulator 172 which regulates the pneumatic pressure supplied to the first port 44 of the pneumatic impulse tool 14. An electrical control unit 174 connected to the pressure regulator 172 dictates the pressure acting at the first port 44 in response to a desired force level selected by the surgeon or technician. The pneumatic control system 12 additionally comprises a vacuum port 176 which connects to a standard vacuum line in the hospital or clinic operating room.

Alternatively, the input port 170 and the vacuum port 176 could be connected to other types of pneumatic pressure and vacuum sources, such as, for example, a compressed gas tank and compressor, and an internal vacuum pump, respectively. However, due to safety and cost considerations, the standard pneumatic supply and vacuum systems existing in the operating room are preferably used.

The input port 170 connects to an internal pressure plenum 178 on the outlet side of the input port 170. The vacuum port 176 similarly connects to an internal vacuum plenum 180 on the input side of the vacuum port 176. The plenums 178, 180 have sufficient size such that the pressurized fluid within the plenums 178, 180 immediately acts on the shuttle 36 when the pneumatic control system 12 places the plenums 178, 180 and the central cavity 26 (FIG. 3) in communication. The plenums 178, 180 supply an instant pressure and vacuum force passing through only control valves and the pneumatic lines 86, 90, thus minimizing the fluidic resistance of the pneumatic system.

As illustrated in FIG. 1, a plurality of solenoid valves, centrally managed by the electrical control unit 174, control the communication between the pressure and vacuum plenums 178, 180 and the first and second ports 44, 46 of the impulse tool 14. The solenoid valves preferably are two-way poppet-type solenoid valves, such as those commercially available from SMC Pneumatics (e.g., valve No. NVS 4114 02 52D), which quickly respond to electrical signals sent by the electrical control unit 174.

A first solenoid valve 182 connects to the pressure plenum 178 and to an ambient air source line 184. The ambient air source line 184 comprises an intake port 186 open to atmospheric air and an in-line, low flow resistant filter 188. The common side ("C") of first solenoid valve 182 connects to a second solenoid valve 190 on its common side ("C"). The second solenoid valve 190, in turn, directly connects to the first port 44 and the second port 46 of the impulse tool 14. A third solenoid valve 192 connects to the vacuum plenum 180 on its common side ("C") and connects to the first port 44 and the second port 46.

The first solenoid valve 182 alternates the pressure acting at the common side of the second solenoid valve 190. The second solenoid valve 190 alternates this pressure between the first port 44 and the second port 46. The third solenoid valve 192 alternates vacuum pressure between the first port 44 and the second ports 46.

All three solenoid valves 182, 190, 192 control the movement of the shuttle during its percussive cycle; the cycle consists of a first stroke (i.e., shuttle travel) from one end of the central cavity 26 to the opposite end and a second reverse stroke back to the initial position. For instance, to drive an orthopedic article in the distal direction, the shuttle 36 starts at the proximal end of the central cavity 26. With all three solenoid valves 182, 190, 192 in their normally open position (designated by "NO"), the pressure plenum 178 communicates with the first port 44 and the vacuum plenum 180 communicates with the second port 46. As a result of the applied pressures, the shuttle 36 accelerates in the distal direction and strikes the drive coupling anvil 122, as discussed in detail below, completing the first cycle stroke. The electrical control unit 174 then switches the solenoid valves 182, 190, 192 to their normally closed position (designated by "NC") which places the first port 44 into communication with the vacuum plenum 180 and places the second port 46 into communication with the ambient air source line 184. As a result, the shuttle 36 moves in the proximal direction to complete the second stroke of the cycle. The cycle can then be repeated.

The second solenoid valve 190 and the third solenoid valve 192 also control the driving direction of the impulse tool 14. To drive an orthopedic article in the proximal direction, the electrical control unit 174 places the first solenoid valve 182 in the normally open position, and the second solenoid valve 190 and the third solenoid valve 192 in their normally closed positions during the first stroke of the cycle. The electrical control unit 174 then reverses the solenoid valves 182, 190, 192 during the second stroke of the cycle. Consequently, the driving force applied during the first cycle stroke drives the orthopedic article in the proximal direction.

The electrical control unit 174 dictates the cycle rate (i.e., the repetition rate of the shuttle 36) of the pneumatic impulse tool 14. The cycle rate preferably ranges between 60 cycles/minute (cyc./min.) and 3000 cyc./min., more preferably ranges between 200 cyc./min and 1200 cyc./min., and most preferably equals about 600 cyc./min.

The electrical control unit 174 also dictates the driving force acting on the shuttle 36. By regulating the pressure within the pressure plenum 178, the control system 174 can dictate the magnitude of force applied by the pneumatic impulse tool 14 on the orthopedic article. The electrical control unit 174 preferably includes a regulator mechanism 194, such as a potentiometer, to add variable control to the pressure regulator 172.

The electrical control unit 174 also preferably comprises a switching mechanism 200 to alternate the control of the solenoid valves 182, 190, 192 between the distal and proximal drive directions. The switching mechanism 200 is preferably remotely located from a console housing the pneumatic control system 12. For example, the switching mechanism 200 could comprises a foot pedal. Alternatively, the switching mechanism 200 could comprise an unobtrusive finger switch on the impulse tool 14, such as a low-profile vacuum bi-lumen positioned on the impulse tool 14 and connected to a vacuum sensitive switch positioned within the pneumatic control system console.

Method of Use

The following elaborates on the previous description for using the pneumatic impulse tool 14 to insert an orthopedic article into or extract an orthopedic article from a bone. The pneumatic impulse tool 14 is connected with the pneumatic control system 12 via the pair of pneumatic lines 86, 90. The first pneumatic line 86, in communication with the second solenoid valve 190, connects to the first port 44 of the pneumatic impulse tool 14 and the second pneumatic line 90 extends between the third solenoid valve 192 and the second port 46.

A surgeon or technician couples the engagement head 120 of the pneumatic impulse tool 14 to an orthopedic article. For instance, the surgeon may attach the pneumatic impulse tool 14 to an orthopedic prosthesis 210, such as, for example, the femoral stem illustrated in FIG. 6, via an adapter 212 such as the type illustrated and described in U.S. Pat. No. 5,045,054, which is hereby incorporated by reference. The surgeon or technician selects an appropriate adapter 212 for the specific type of prosthesis 210, accounting for the particular implant angle, ball size, hole size, etc. The engagement end 120 of the impulse tool 14 is attached to the adapter 212 via the extender 214. The adapter 212 is then attached to the proximal end of the prosthesis 210. Although FIG. 6 illustrates the impulse tool 14 generally aligned with a cord line of the prosthesis 210, it is understood that the impulse tool 14 could be coupled to the prosthesis 210 at any desired angle.

The following discussion of the pneumatic impulse tool 14 and its operation precedes with respect to the insertion and extraction of a prosthesis 210 from a femur during hip surgery. It should be understood, however, that the following examples are intended for purpose of illustration and are not to be construed as in any way limiting the scope of the present invention.

The surgeon (or technician per the surgeon's instructions) selects the force setting for driving the prosthesis into the femoral canal, according to the "feel" desired by the surgeon, by adjusting the regulator mechanism 194 of the electrical control unit 174. Thus, the pneumatic impulse apparatus is ergonomically adjustable for each orthopedic surgeon. The surgeon also selects the drive direction and cyclic rate of the impulse tool 14.

As mentioned above, the first cycle stroke begins with the shuttle 36 juxtaposing the anvil surface 76 of the proximal end plug 38. To apply an impulse force on the prosthesis 210 and thus drive the prosthesis 210 into the femoral canal (not shown), the first and second solenoid valves 182, 190 open to supply pneumatic pressure through the first port 44. Simultaneously, the third solenoid valve 192 opens to supply a vacuum pressure on the second port 46. The fluid (air) in the duct 32 and the central cavity 26 on the distal side of the shuttle 36 is drawn through the second port 46, thereby applying a vacuum force on the shuttle 36. The resultant pressure differential on the opposite ends of the shuttle 36 propels the shuttle 36 through the central cavity 26 in the distal direction.

As described above, a boundary of air is formed between the shuttle 36 and the interior surface 64 of the central cavity 26 as the shuttle 36 travels through the central cavity 26. The shuttle 36 glides on the air boundary which reduces friction between the shuttle 36 and the interior surface 64. Consequently, frictional forces, acting against the pneumatic force, are reduced.

The shuttle 36 impacts against the anvil surface 124 of the drive coupling anvil 122, imparting its momentum through the drive coupling 56 to the prosthesis 210. The shuttle 36 advantageously only drives the drive coupling 56, as opposed to the entire pneumatic impulse tool 14, to maximize the energy transferred to the prosthesis 210.

The shuttle's momentum at impact applies a driving force on the prosthesis 210 great enough to initially overcome the friction force between the prosthesis 210 and the host cancellous bone (not shown). Consequently, the prosthesis 210 advances into the bone by a dimensional increment which is proportional to the resultant force in the distal direction (i.e., the positive difference between the driving force minus the opposing friction force) over the impulse period (i.e., the duration of the collision between the shuttle 36 and the drive coupling anvil 122).

The applied driving force is preferably sufficiently large to produce inertial fixation in the host bone. That is, the impulse force driving the prosthesis 210 into the bone is so quickly applied and is sufficient in magnitude to rapidly drive the prosthesis 210 in the distal direction without moving the bone by an meaningful amount; the femur, and surrounding leg, remain generally stationary, fixed by their own inertia. The ratio between the force applied to the prosthesis and the force transferred from the prosthesis 210 to the bone should be at least 5 to 1, and more preferably be 10 to 1, in order to meaningfully fix the leg by its own inertia. Consequently, less force is transferred to the bone and leg, reducing the trauma the patient experiences in the leg and reducing the arduousness of the procedure.

Figure 7:
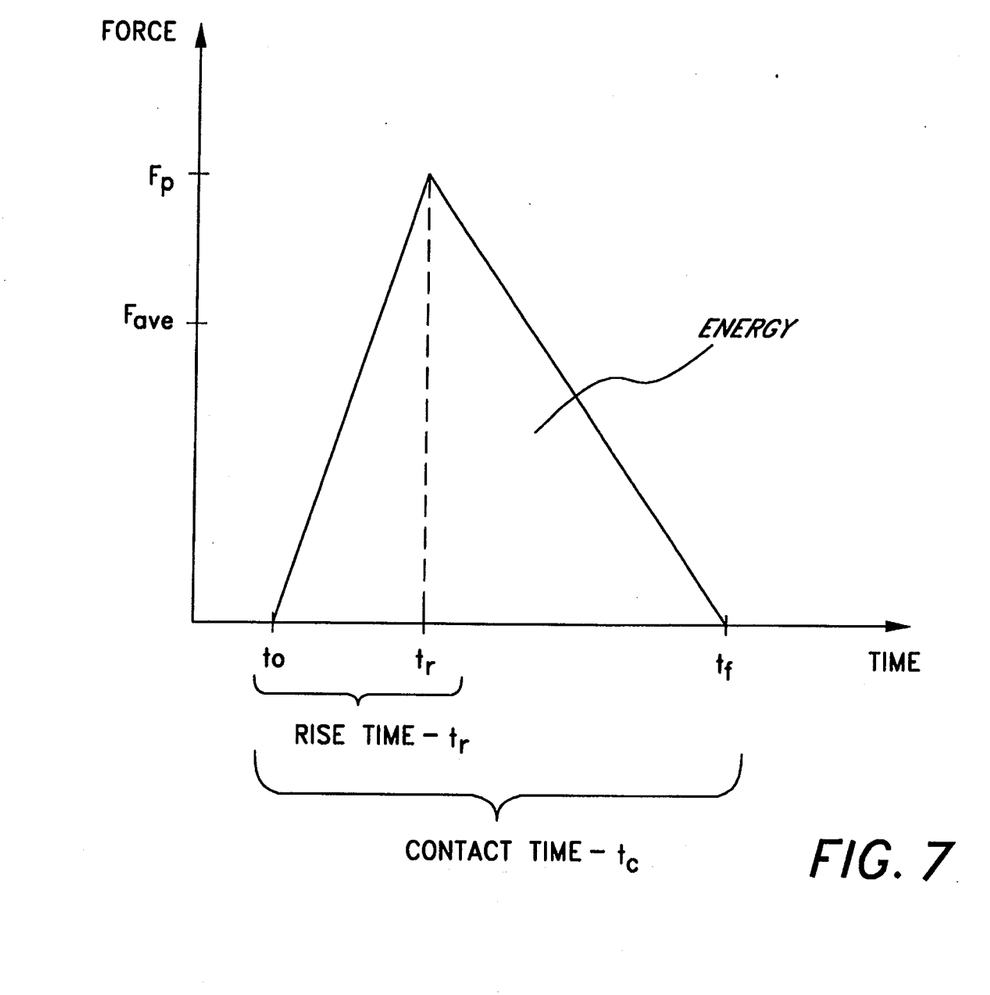
FIG. 7 is an impulse force graph plotted against time illustrating the rise and fall rates of the impulse force.

FIG. 7 illustrates a graph of a driving or impulse force plotted against time. The impulse force begins the moment that the shuttle 36 contacts the anvil 122 of the drive coupling 56 at $t_0$. The impulse force then increases in magnitude over a rise time period $t_r$ and reaches a peak force $F_p$. After reaching the peak force $F_p$, the impulse force deceases in magnitude to zero when the shuttle 36 ceases contacting the anvil 122 at $t_f$ during the initial impact. The total contact time $t_c$ between the shuttle 36 and the anvil 122 during an initial impact is the period between $t_0$ and $t_f$. Although FIG. 7 illustrates the impulse force increasing and decreasing linearly over the total contact time $t_c$, it is understood that the impulse force does not increase and decrease precisely linearly.

The positive rate of impulse force transfer (i.e., "the rise rate") between the shuttle 36 and the drive coupling anvil 122 is equal to $$\frac{\sqrt{2EM}}{t_r^2}$$

where E=the kinetic energy of the shuttle at impact (lb.in.), M=the mass of shuttle (lb.sec$^2$/in.) and $t_r$=the rise time (sec.). Through empirical and analytical analysis, it has been determined that in order to achieve meaningful inertial fixation of the host bone, the impulse force preferably has a rise time $t_r$ equal to less than 100.0 microseconds ($\mu$sec.), and more preferably equal to less than 10.0 $\mu$sec. Additionally, the total contact time $t_c$ between the shuttle 36 and the drive coupling anvil 122 during the initial impact should be limited to minimize the total energy transferred to the prosthesis 210. The total contact time $t_c$ is preferably less than 300.0 $\mu$sec., and is more preferably less than 30.0 $\mu$sec.

The rise time $t_r$, as well as the collision time $t_c$, are proportional to the mass M of the shuttle 36. Heavy objects tend to stay in contact longer than lighter objects, and heavy objects tend to transfer momentum slower than lighter objects. However, the shuttle 36 should have sufficient mass to produce a desired magnitude of impulse force at impact.

The impulse force and corresponding kinetic energy required to overcome the friction force between the prosthesis 210 and the host bone are proportional to the mass M of the shuttle 36 (F =MV/$t_c$ and E=½ MV$^2$, where V is the velocity of the shuttle 36 at impact with the drive coupling anvil 122). For instance, a shuttle 36 having a diameter of 0.750 inch has about twice the kinetic energy at impact that a shuttle 36 having a diameter of 0.500 inch has at impact, where the distance of travel and the pneumatic force applied to the shuttle 36 are identical in each case. Similarly, a shuttle 36 having a diameter of 1.000 inch has about four times the kinetic energy at impact that by a shuttle 36 having a diameter of 0.500 inch has at impact.

In addition, because the impulse force is not applied instantaneously, but instead is applied over the rise time $t_r$ period, the peak force $F_p$ (and the total energy) required to overcome the opposing friction force must be at least about 1.5 times greater the opposing friction force. Thus, the mass M of the shuttle 36 must be optimized to produce the desired rise time $t_r$ and to produce the necessary peak force $F_p$ required to overcome the opposing friction force.

The peak force $F_p$ is also proportional to the velocity of the shuttle 36 at impact (F=MV/$t_r$). The velocity of the shuttle 36 is a function of the distance of travel of the shuttle 36 moving under a constant force applied by the pressure differential within the central cavity 26. However, the distance of shuttle travel—that is, the distance between the proximal end anvil 76 and the drive coupling anvil 122 defined by the central tube 24—should not be too long; the longer the impulse tool 14 the more leverage the surgeon has to accidentally break the host bone by applying a transverse force to the proximal end of the pneumatic impulse tool 14. Moreover, too long of a length will impede the maneuverability of the pneumatic impulse tool 14. The length of the central tube 24 should also be less than the length required for the shuttle 36 to reach its terminal velocity; a length greater than this length would not produce greater energy and thus would be superfluous.

Additionally, the peak force $F_p$ depends upon the constant pneumatic force applied to the shuttle 36. When using the existing pneumatic sources in the operating room, as preferred, the maximum pneumatic force is limited to the pressure difference between the pneumatic pressure line (usually 70 lbs./inch$^2$ (psi) above an ambient pressure) and the vacuum line (usually 15 psi below an ambient pressure). Thus, the maximum constant pneumatic pressure is typically 85 psi. However, the pneumatic impulse tool 14 preferably is designed to operate at a constant pneumatic pressure differential substantially less than the maximum pneumatic pressure differential in order to provide some adjustment in the level of driving force applied to the prosthesis 210, and, thus, some adjustment in the increment that the prosthesis 210 travels per cycle.

The high acceleration of the shuttle 36 not only produces inertial fixation, but also provides more precise control of the attached orthopedic article during surgical procedures. The high acceleration of the shuttle 36 enables a high repetition rate of the shuttle 36. As a result, a surgeon can select a minimal force which produces only a small increment of movement (e.g., 0.010 inch) of the orthopedic article, but the high repetition rate produces a desired total movement of the orthopedic article within a workable period of time. For instance, the surgeon could select a small driving force and a high repetition rate to produce 1.0 millimeter of advancement per second of the orthopedic article into or out of the host bone. The small increment of movement, however, enables precise control over the orthopedic article. In addition, the high acceleration of the shuttle 36 provides a sufficient shearing and cutting force when used with tool bits.

Thus, the mass M of the shuttle 36 and the length of the central tube 24 between the proximal end plug 38 and the drive coupling 56 should be selected to: (1) apply a peak force $F_p$ at least 1.5 time greater that the opposing force, (2) under a constant pneumatic pressure differential substantially less than the available maximum pneumatic pressure differential, (3) over a rise time $t_r$ equal to less than 100.0 $\mu$sec. and (4) apply the impulse force over a total contact time $t_c$ equal to less than 300.0 $\mu$sec. With the foregoing parameters in mind, it is contemplated that those skilled in the art could design the pneumatic impulse tool 14 to produce a desired force to overcome friction or to break a bond between the prosthesis and cancellous bone or PMMA cement and to produce meaningful inertial fixation of the host bone.

Referring back to FIG. 3, the spring 60 compresses as the shuttle 36 drives the anvil 124 in the distal direction at impact. The spring 60 returns the anvil 124 to its initial position after the shuttle's momentum has transferred to the prosthesis 210.

At this stage of the cycle, the electrical control unit 174 switches the solenoid valves 182, 190, 192 to their normally closed positions to supply the second port 46 of the pneumatic impulse tool 14 with ambient pressure and to supply the first port 44 with a vacuum pressure. The resultant pressure differential pushes the shuttle 36 in the proximal direction until it strikes the proximal end plug anvil 76. The impulse force applied by the shuttle in the proximal direction, however, is substantially less than the impulse force applied in the distal direction such that over the entire cycle, the prosthesis 210 is driven in the distal direction into the femoral canal. The impulse force applied as the shuttle 36 strikes the proximal end anvil 76 is preferably slightly greater than the friction force between the prosthesis and the host cancellous bone. Thus, the prosthesis 210 moves by a small increment (e.g., 0.005 inch) in the proximal direction to relief hoop stress (i.e., radial and tangential stresses) in the host bone. If a broach, rasp or tool bit is used with the impulse tool 14, this slight reverse movement of these articles clear outs or breaks off bone fragments.

With the shuttle 36 in its initial position juxtaposing the proximal end anvil surface 76, the pneumatic impulse tool 14 is ready to begin a second cycle identical to the cycle described above.

To extract a prosthesis 210, which is either held in place by cancellous bone ingrowth or by PMMA cement, the surgeon or the technician couples the pneumatic impulse tool 14 to the prosthesis 210 as described above. The surgeon or technician then reverses the drive direction of the impulse tool 14 via the switching mechanism 200.

In the reverse mode (i.e., applying a drive force in the proximal direction), the impulse force of the shuttle 36 impacting on the proximal end anvil 76 is substantially greater that the impulse force of the shuttle 36 striking the drive coupling anvil 122. For instance, it has been determined that the peak force $F_p$ applied in the proximal direction operating under a constant pneumatic pressure of 85 psi should be about 1800 lbs. to give an average driving force of about 1200 lbs., which is believed sufficient to break the typical cancellous bone ingrowth. Thus, the desired rise rate should be about 18 lbs./$\mu$sec. The shuttle 36, under a constant pneumatic pressure of about 15 psi on the latter cycle stroke, strikes the drive coupling anvil 122 with substantially less force. The force produced in the latter cycle stroke is typically less than the friction force between the prosthesis and the host cancellous bone, and, thus, the prosthesis remains generally stationary during the latter cycle stroke in the reverse mode.

Figure 8:
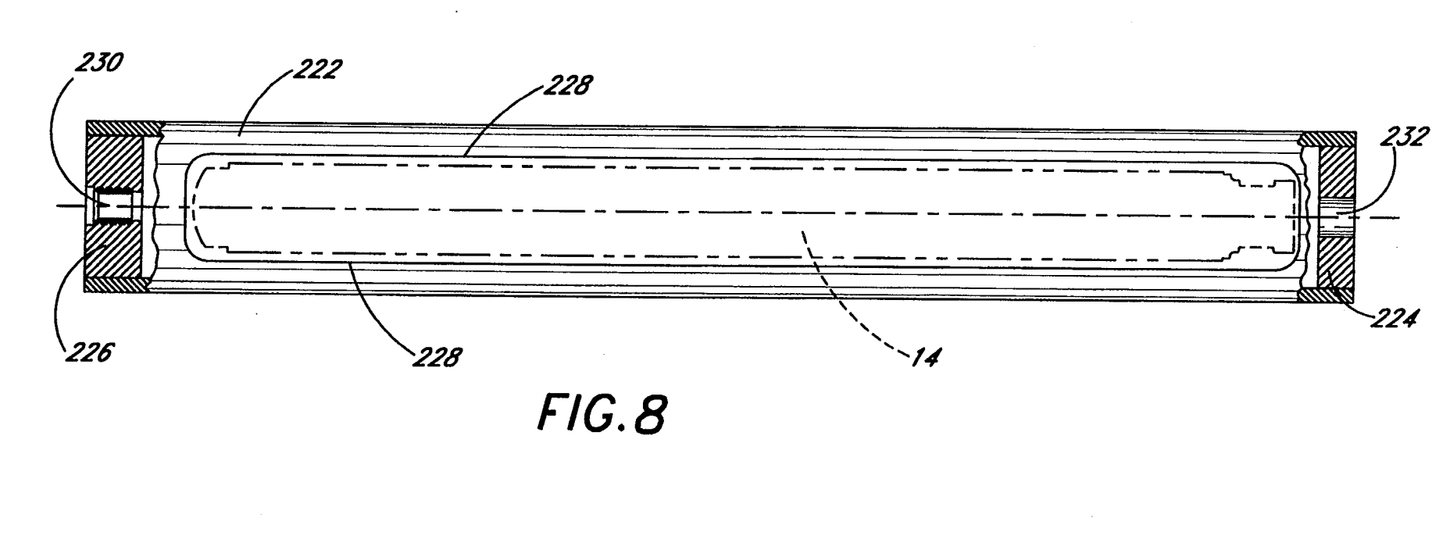
FIG. 8 is a side elevational view of an adapter used with the impulse tool of FIG. 1.

The pneumatic impulse tool 14 can alternatively be used with a low mass adapter 220, as illustrated in FIG. 8, to extract an orthopedic article (e.g., rods, nails, prosthesis) from the host bone. The low mass adapter 220 comprises a tubular body 222 closed at its ends by a proximal bulkhead 224 and a distal bulkhead 226. The tubular body 222 defines an elongated aperture 228 which opens into the interior of the tubular body 222. The aperture 228 is sufficiently sized to receive the pneumatic impulse tool 14 and to allow clearance for the pneumatic lines 86, 90.

The distal bulkhead 226 defines a junction component and preferably defines a quick connect junction component. More preferably, the distal bulkhead 226 defines a female component 230 configured in accordance with the above description of the female component 140 of the engagement end 120. The female component 230 of the distal bulkhead 226 is preferably concentrically positioned about a longitudinal axis of the tubular body 222. The proximal bulkhead 224 defines a hole which is likewise concentrically positioned about the 232 longitudinal axis of the tubular body 222.

The tubular body 222 and the bulkheads 224, 226 are preferably formed of a stainless steel, such as a 400 series or 17-4 series stainless steel, because of its relative biocompatibility and its high yield strength. The bulkheads 224, 226 are then preferably electron-beam welded or attached by other means to the tubular body 222.

In use, the impulse tool 14 is placed within the tubular body 222 through the aperture 228. The engagement end 120 of the impulse tool 14 is secured to the proximal bulkhead 224 by a threaded thumb screw (not shown) passing through the proximal bulkhead hole 232. The distal bulkhead 226 is then coupled to the orthopedic article (e.g., the prosthesis 210) as described above.

The impulse tool 14 thus drives only the drive coupling 56 and the low mass adapter 220 when extracting the orthopedic article. Consequently, the impulse force generated drives a combined mass of the drive coupling 56 and adapter 220, which is less than the entire mass of the impulse tool 14, to maximize the energy transferred to the orthopedic article.

The small size, light weight and symmetric design of the pneumatic impulse tool 14 makes it extremely maneuverable during surgery. The symmetric design and in-line coupling with the orthopedic article also maximizes the driving or extracting force on the orthopedic article and improves the surgeon's control over the orthopedic article. In addition, the impulse tool's simple design and minimal number of parts minimizes material and manufacturing costs. Thus, the pneumatic impulse tool 14 could be made inexpensive enough to become disposable or recyclable, thereby enhancing the reliability and sterility of the impulse tool 14.

Although this invention has been described in terms of a certain preferred embodiment, other embodiments apparent to those of ordinary skill in the are also within the scope of this invention. Accordingly, the scope of the invention is intended to be defined only by the claims which follow.

What is claimed is:

1. A method of implanting an orthopedic prosthesis into or extracting an orthopedic prosthesis from a host bone, said method comprising the steps of:

providing a reciprocating mass hammer comprising a shuttle movably disposed within an elongated bore, said hammer further comprising an anvil positioned at a distal end of said bore and connected to an engagement head of said hammer;

positioning an orthopedic prothesis in a medullary canal of a host bone such that a frictional force opposes movement of the prosthesis relative to the host bone;

coupling said engagement head of said reciprocating hammer to a proximal end of said prosthesis;

accelerating said shuttle through said elongated bore;

striking said anvil with said shuttle to produce an impulse force sufficient to overcome said frictional force opposing movement of said prosthesis; and imparting a peak level of said impulse force from the shuttle to the anvil over a rise time period equal to or less than about 100 $\mu$sec.

2. The method of claim 1 additionally comprising the step of selecting said shuttle to have a sufficiently minimized mass and selecting said elongated bore to have a sufficiently long length, such that said impulse force produced by said shuttle traveling through said elongated bore and striking said anvil is sufficient to overcome said frictional force opposing the insertion of the orthopedic prosthesis into or the extraction of the orthopedic prosthesis from the host bone with said peak force being reached over a rise time of less than 100 $\mu$sec.

3. The method of claim 1 additionally comprising the step of reducing friction between said shuttle and said elongated bore by producing an air bearing boundary layer between said shuttle and said elongated bore as said shuttle travels through said elongated bore.

4. The method of claim 1, wherein said step of striking said anvil comprises the step of contacting said anvil with said shuttle for a contact time equal to or less than about 300 $\mu$sec.

5. The method of claim 1, wherein said shuttle contacts said anvil for a period equal to or less than about 30 $\mu$sec.

6. The method of claim 1, wherein said peak level of said impulse force is imparted over a rise time period equal to or less than about 10 $\mu$sec.

7. The method of claim 1 additionally comprising the step of selecting said shuttle to have a sufficiently minimized mass and selecting said elongated bore to have a sufficiently long length such that said impulse force is at least five times greater than a resultant force transferred from said orthopedic prosthesis to the host bone.

* * * * *